United States Patent
Barberio

(10) Patent No.: US 8,777,883 B2
(45) Date of Patent: *Jul. 15, 2014

(54) SURGICAL CAST VENTING DEVICE AND MATERIAL

(75) Inventor: Alessandro Aldo Barberio, Aurora (CA)

(73) Assignee: Alessandro Aldo Barberio, Aurora, Ontario (CA)

( * ) Notice: Subject to any disclaimer, the term of this patent is extended or adjusted under 35 U.S.C. 154(b) by 923 days.

This patent is subject to a terminal disclaimer.

(21) Appl. No.: 12/448,897

(22) PCT Filed: Jan. 9, 2008

(86) PCT No.: PCT/CA2008/000029
§ 371 (c)(1),
(2), (4) Date: Jul. 15, 2009

(87) PCT Pub. No.: WO2008/083477
PCT Pub. Date: Jul. 17, 2008

(65) Prior Publication Data
US 2011/0152735 A1 Jun. 23, 2011

Related U.S. Application Data

(60) Provisional application No. 60/897,350, filed on Jan. 25, 2007, provisional application No. 60/929,615, filed on Jul. 5, 2007.

(51) Int. Cl.
*A61F 5/00* (2006.01)
*A61F 5/37* (2006.01)

(52) U.S. Cl.
USPC .......................................... 602/14; 128/881

(58) Field of Classification Search
USPC ........... 602/14, 10, 13, 76, 79, 60, 61, 1, 2, 5, 602/20; 607/108, 112; 604/307; 2/239, 409, 2/59, 61, 90, 91; 66/178 R, 196; 128/881, 128/846, 869, 878

See application file for complete search history.

(56) References Cited

U.S. PATENT DOCUMENTS

| | | | |
|---|---|---|---|
| 2,373,802 A | 4/1945 | Anderson | |
| 3,850,167 A | 11/1974 | Seeley | |
| 4,898,160 A * | 2/1990 | Brownlee | 602/14 |
| 5,468,219 A * | 11/1995 | Crippen | 602/6 |
| 5,507,792 A * | 4/1996 | Mason et al. | 607/104 |
| 5,916,184 A * | 6/1999 | McKeel | 602/6 |
| 6,547,751 B1 | 4/2003 | Barberio | |
| 6,616,622 B1 * | 9/2003 | Barberio | 602/14 |
| 7,229,425 B2 * | 6/2007 | Dunagan | 602/14 |
| 7,250,034 B2 * | 7/2007 | Barberio | 602/14 |

* cited by examiner

*Primary Examiner* — Patricia Bianco
*Assistant Examiner* — Tarla Patel
(74) *Attorney, Agent, or Firm* — Young Basile Hanlon & MacFarlane P.C.

(57) ABSTRACT

A surgical cast venting material comprises a waterproof, flexible substrate made of a plastics material and having first and second sides. The first side has a plurality of shallow, concave recesses distributed over the substrate and spaced-apart from one another while the second side has a plurality of protrusions distributed across the substrate. The substrate is perforated with a plurality of small holes distributed across its length and width. Also, a surgical cast venting device is disclosed for venting a bent region of a patient's limb. It has a flexible, central portion that can cover a major part of the bent region of the limb including opposite side surfaces and a front or rear surface. The device also has flexible connecting straps extending from two corners of the central portion.

9 Claims, 8 Drawing Sheets

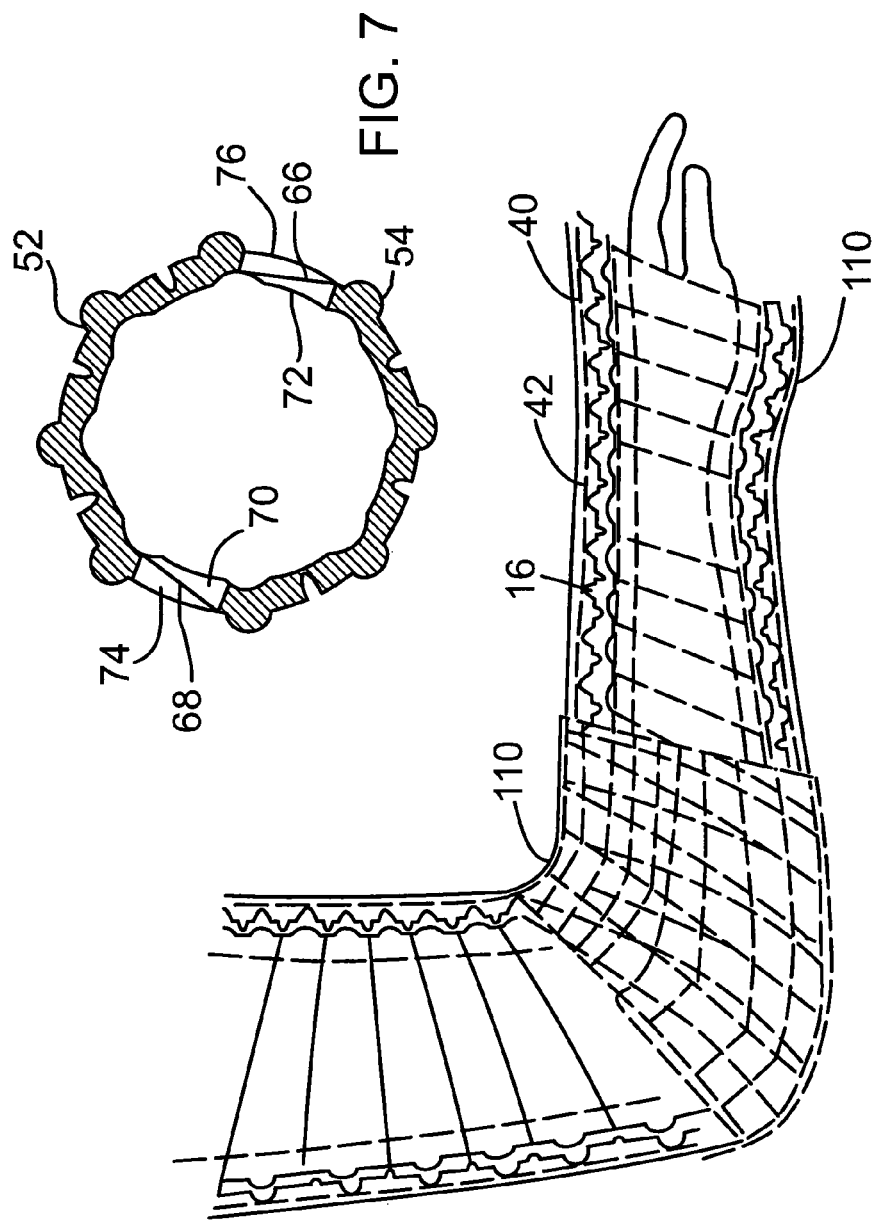

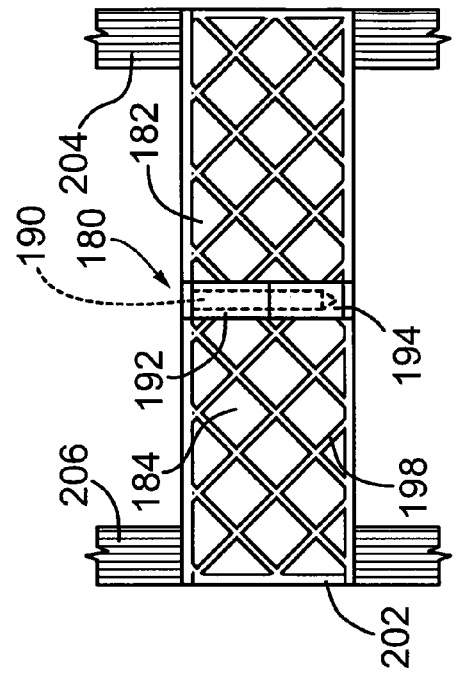
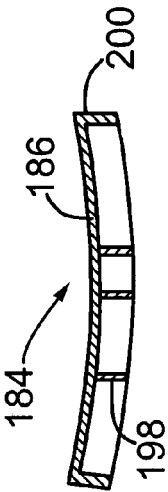
FIG. 9b
FIG. 10
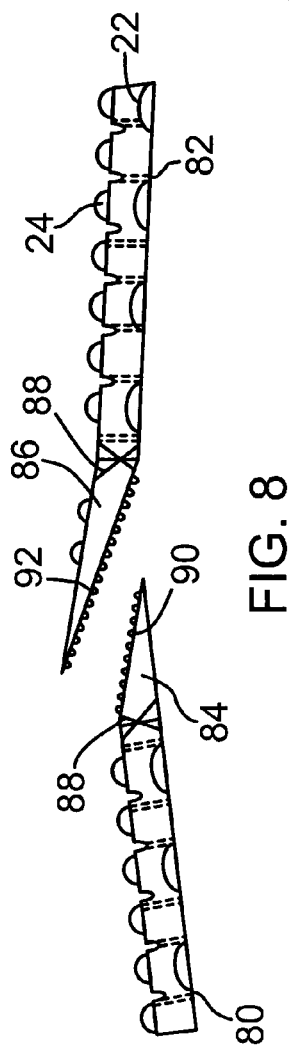
FIG. 8
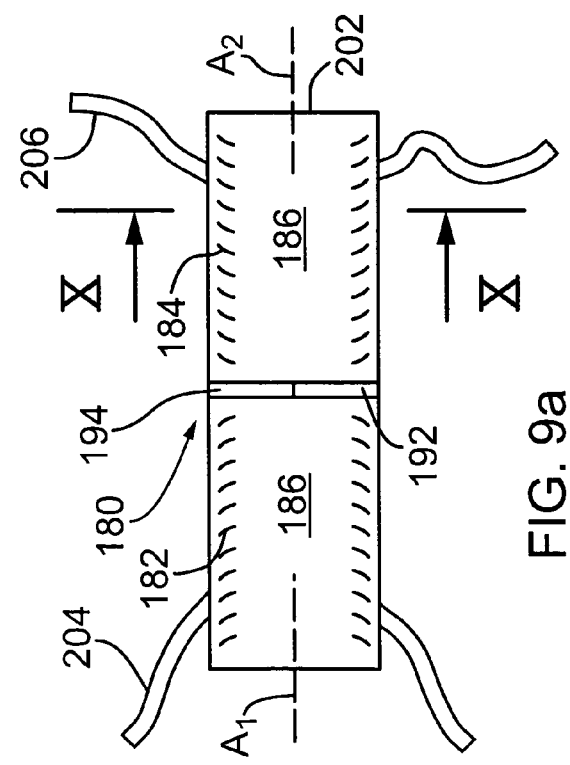
FIG. 9a

SURGICAL CAST VENTING DEVICE AND MATERIAL

CROSS-REFERENCES TO RELATED APPLICATIONS

This application is the National Stage of International Application No. PCT/CA2008/000029, filed Jan. 9, 2008, which claims the benefit of U.S. Provisional Application No. 60/897,350, filed Jan. 25, 2007, and claims the benefit of U.S. Provisional Application No. 60/929,615, filed Jul. 5, 2007.

FIELD OF THE DISCLOSURE

This application claims priority under 35 USC 119(e) to provisional applications 60/897, 350, filed 9 Jan. 2007 and 60/929,615, filed 5 Jul. 2007.

This invention relates to venting materials and venting devices for placement under surgical casts for humans and animals as well as devices for supporting fractured limbs of human patients and animals, particularly devices which can be used in conjunction with surgical casts.

SUMMARY

A variety of devices for venting surgical casts have been proposed in the past but many of these devices have not met with commercial success. The known devices may have tubes which form air passageways to permit air circulation between the rigid cast exterior and the patient's skin. One such venting device is shown in U.S. Pat. No. 4,898,160 dated Feb. 6, 1990, this device including a multi-channel, flexible form that is placed adjacent to the skin and is able to adapt to the contour of the body part. Sloping walls of the channels are formed with a plurality of spaced-apart apertures. This venting device can be placed over a cast stockingette which is first placed on the body part.

In Applicant's U.S. Pat. No. 6,616,622, issued Sep. 9, 2003, a number of different versions of devices for venting surgical casts are described. One version has an elongate, porous woven fabric strip to which are attached a plurality of flexible, elongate tubes with holes distributed along their respective lengths. The strip can be wound around part of a human's body or an animal's body prior to application of the cast. The fabric strip comprises a cotton gauze material.

U.S. Pat. No. 5,916,184 dated Jun. 29, 1999 describes an orthopedic airflow and waterproof cast padding material in the form of an elongate pad with top and bottom surfaces and an inside edge with an overlap region. The pad is made from water and air impermeable material such as thermal foam closed cell polyethylene. This known pad can be helically wrapped around a fractured limb to form a cast pad and an immobilizing waterproof cast when wrapped with special casting tape. A plurality of cushions project from one surface of the elongate pad between the outside edge and the overlap region and these cushions are placed against the skin as the pad is wrapped.

Experiments conducted by the applicant on various forms of venting devices have shown that key factors for their success include their ease of use by medical practitioners and the amount of comfort that is provided by the venting device or by the venting material after it has been applied and is in position below the rigid cast. Another significant factor is the ability of the venting device to fit closely on the limb to which it is being applied and in a manner which will not create pressure points on the skin and other regions of discomfort.

There is a need for an improved surgical cast venting material that can be manufactured at a reasonable cost and that is relative easy for medical practitioners to apply to a limb before the rigid cast is formed. An improved venting material should provide adequate venting of the skin which is covered by the material and the cast.

There is a further need for a surgical cast venting device which can be easily applied and used on a section of a patient's limb having a bend therein, for example, the elbow area of an arm, the knee area of a leg, and the ankle area. Such a venting device must be relatively inexpensive to manufacture while at the same time being capable of closely fitting the patient's limb, including the section of the limb which is bent.

There is also a need in the medical field for a device for supporting a fractured limb of a patient while, for example, the aforementioned venting material is in place or is being put in place and prior to application of the material which will harden to form the rigid cast. The present venting material, because it is made of a flexible material, cannot normally be used to support the fractured limb, particularly in the region of the fracture itself, and therefore it is desirable to provide a proper, rigid support which will maintain or help maintain the fractured bone sections in place (and thereby keep the patient reasonably comfortable) during the process of forming the cast about the limb.

According to one embodiment of the invention, a surgical cast venting material comprises a flexible, waterproof substrate formed of a plastics material having a first side, an opposite second side, a length, and a width. The first side has a plurality of shallow, concave recesses distributed across the length and the width of the substrate and spaced apart from one another. The second side has a plurality of protrusions distributed across the length and width of the substrate and spaced-apart from one another. Each of at least a majority of the protrusions are located directly opposite a respective one of the concave recesses. The substrate is perforated with a plurality of relatively small holes distributed across the length and width of the venting material.

In an exemplary version of this venting material, the plastics material is ethyl vinyl acetate and has an initial thickness of about 3 mm prior to the substrate being molded to form the recesses and protrusions.

According to another embodiment of the invention, a surgical cast venting device for venting a region of a patient's limb which includes a first section of a patient's limb having a bend therein, includes a flexible main, central portion adapted to cover a major part of the first section of the patient's limb having the bend therein, including opposite side surfaces of the limb and a front or rear surface extending between the side surfaces. The venting device also includes two elongate, flexible connecting strips extending from and connected to two corners of the central portion located on opposite sides of the central portion. Each strip is adapted and arranged to be wrapped in a spiral manner around a respective one of second and third sections of the patient's limb, these sections being located at opposite ends of the first section and adjacent thereto. At least the central portion has a first side and an opposite second side and the first and second sides during use of the venting device are positioned on opposite sides of the first section of the patient's limb. The first and second sides are formed to permit air circulation under a surgical cast that is formed over the venting device when the venting device has been arranged on the first, second and third sections of the patient's limb so as to substantially cover at least the major part of the first section of the patient's limb.

In an exemplary version of this embodiment, the central portion and the connecting strips are made of a waterproof, flexible substrate formed of a plastics material having an inner side and an outer side. The inner side has a plurality of shallow, concave recesses distributed over the substrate and the outer side has a plurality of protrusions distributed over the substrate. The recesses and protrusions help to provide the air circulation during use of the venting device.

According to another embodiment of the invention, a device for supporting a fractured limb of a patient includes two supporting plates adapted to and sized to support the limb on one side of the fracture prior to application of a surgical cast. A connector for adjustably connecting the two adjacent ends of the supporting plates together is also provided, this connector being movable from a locked position where no relative movement between the supporting plates occurs and an adjusting position which allows relative pivotal movement between the central longitudinal axes of the supporting plates. During use of the supporting device, a surgical cast can be formed around the supporting device and the fractured limb while the supporting device is secured to one side of the fractured limb with the connector in the locked position.

In an exemplary version of this device, each supporting plate has an inside surface which is contoured so as to have a concave shape substantially matching to the contour of the fractured limb in the region of the fracture and on the one side of the fracture where the supporting device is to be used.

Further features and advantages of the various embodiments of the invention will become apparent from the following detailed description taken in conjunction with the accompanying drawings.

BRIEF DESCRIPTION OF THE DRAWINGS

In the drawings,

FIG. 2b is a partial view of the opposite side of the cast venting material of FIG. 2a;

FIG. 6 is a side view, partly in cross-section, showing an arm enclosed in a venting arrangement and a tubular stockingnette;

FIG. 7 is a transverse cross-section of the molded venting sections of FIG. 5, this view taken along the line VII-VII;

FIG. 8 is a cross-sectional detail of two adjacent sections of venting material showing the use of wedge-shaped edge sections and how these edge sections can be attached;

FIG. 9a is a top view of a device for supporting a fractured limb;

FIG. 9b is a bottom view of the device of FIG. 9a, this view showing connecting straps in an alternate position;

FIG. 10 is a transverse cross-section of the supporting device of FIGS. 9a and 9b, this view being taken along the line X-X of FIG. 9a;

DETAILED DESCRIPTION

Figure 1:
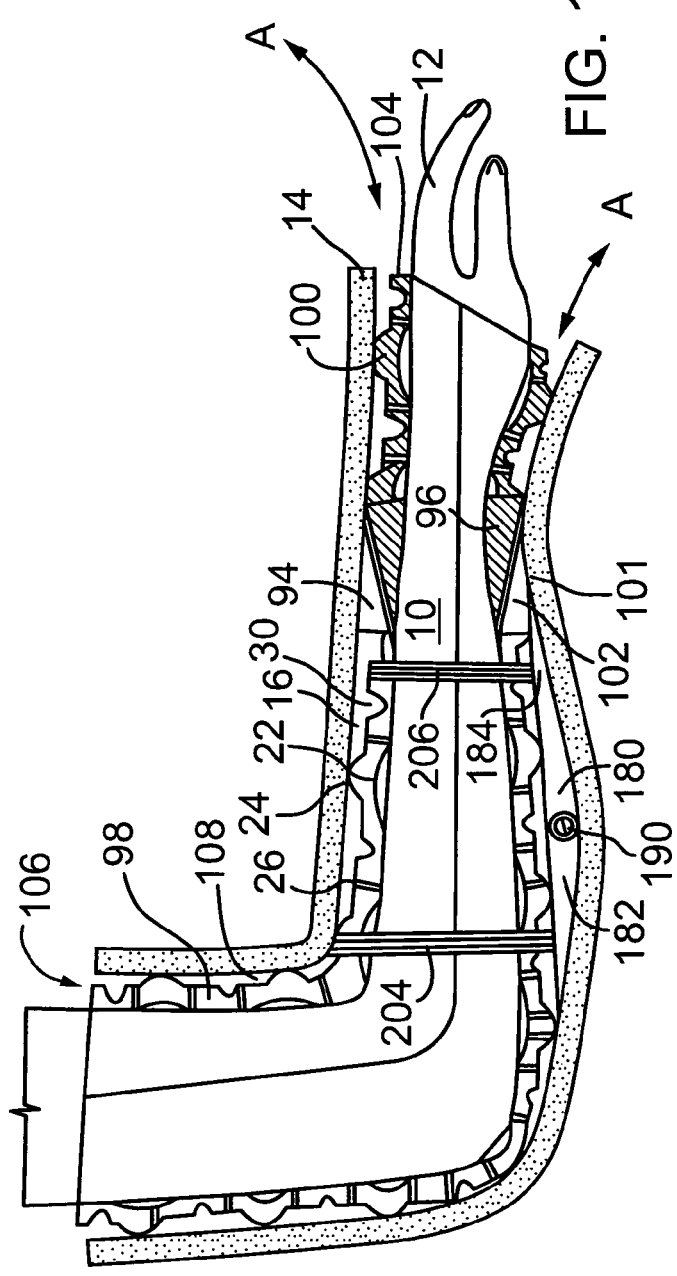
FIG. 1 is a vertical cross-section showing a fractured arm enclosed in cast venting material surrounded by a surgical cast, this cross-section taken along centerlines of the cast.
Figure 2B:
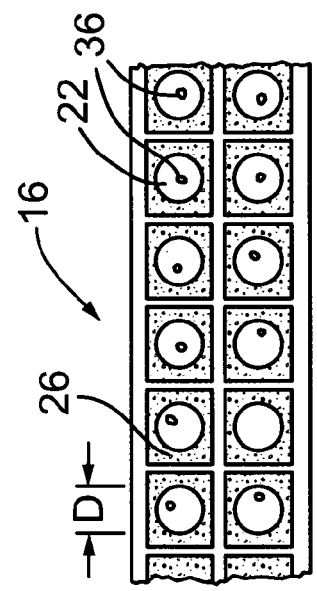
Figure 2A:
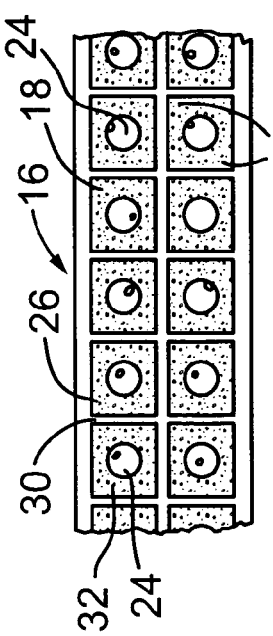
FIG. 2a is a partial view showing one side of surgical cast venting material according to one embodiment of the invention.

Shown in FIG. 1 is a fractured limb of a patient, in this case, an arm 10 having a hand 12. In order to heal the fracture (not shown), it is a well known medical practice to enclose the arm in a rigid surgical cast 14. The cast itself can be of standard construction and accordingly a detailed description herein is deemed unnecessary. Prior to application of the cast material, there can be applied, in accordance with the invention, a layer of cast venting material indicated generally at 16 which can be fitted over the entire skin area which is to be enclosed by the cast. FIGS. 2a and 2b illustrate outer and inner surfaces of one embodiment of this venting material which is a waterproof, flexible substrate formed of a plastics material having a second or outer side 18 which faces towards the cast and a first or inner side 20 which faces the skin and which, in some cases of use, can lie immediately adjacent the skin or, in alternative cases, can be separated from the skin by a thin, fabric material which can be either hydrophilic or hydrophobic or by an inner layer of stockingnet. A common material applied to the skin prior to application of the venting layer is cotton fabric or cotton gauze. The venting substrate or material 16 also has a length and a width, both of which can vary, depending upon the manner in which the venting material is to be applied to the patient, the size of the body part or limb which is to be covered by the material, and other factors. The substrate has a material thickness of about 1 mm when molded or pressed to the required shape, not including the height of protrusions formed thereon. Prior to the molding or heat forming step, the plastics material forming the venting material can have an initial thickness of about 3 mm and, in an exemplary form of the venting material, it is made of ethyl vinyl acetate (EVA). The venting material is formed with a plurality of shallow, concave recesses 22 on the first side 20, these recesses being distributed across the length and the width of the substrate and spaced-apart from one another. In one exemplary version of the material, the diameter D of the edge of the recess is about 7 to 8 mm. The maximum depth of each recess can be in the order of 2-3 mm. The second side 18 has a plurality of protrusions 24 distributed across the length and width of the substrate and spaced apart from one another.

These protrusions can be circular when seen in plan view as shown but other shapes such as square or elliptical are also possible. Each of at least a majority of protrusions 24 are located directly opposite a respective one of the recesses 22 as can be seen from FIG. 1. In fact, in an exemplary embodiment, all of the protrusions 24 are located directly opposite a respective one of the recesses. In this way, the thickness of the substrate is generally retained so that its strength and integrity throughout its length and width is generally uniform.

In addition, the venting material is perforated with a plurality of relatively small holes 26 which are distributed across the length and width of the venting material as well. These holes can be formed in the plastics material before it is molded or shaped to form the protrusions and recesses and, in an exemplary form of the material, the small holes prior to the shaping or molding process are spaced 2 mm apart both in the lengthwise and widthwise direction of the material. For ease of illustration, the holes 26 are shown separated apart a greater distance than 2 mm in FIGS. 1, 2a and 2b.

In order to increase the ability of the venting material to bend and flex, a criss-crossing pattern of grooves 30 is formed in the material during the molding or heat forming process. Extending between the grooves and the protrusions are relatively flat regions 32 which, in the embodiment of FIG. 2a, each have a square perimeter. Instead of being relatively flat, each region 32 can be arc shaped so as to form a convex surface extending between the protrusion and the surrounding grooves. As shown, the grooves are elongate and can extend both the width and the length of the plastics material. In addition to adding flexibility, the grooves 30 can also serve as air passages to assist in the circulation of air under the cast. Another advantage of the grooves 30 is that they further the ability of the venting material to be stretched around the limb or other body part, if required, for a good fit. The provision of the grooves also provides more room for air to be present in and to circulate in the close fitting area between the patient's skin and the cast. Although the grooves 30 shown in the drawings are shown as a series of transverse and longitudinal grooves extending perpendicular to each other, it is also possible for the transversely extending grooves to extend at an obtuse or acute angle to the other series of grooves which extend generally longitudinally. If the venting material is provided in an elongate strip form for wrapping in a spiral manner about a fractured limb, for example, the width of the strip can be about 2 cm and the length of the strip can be plus or minus 40 cm. The use of a strip form of venting material can be advantageous where a body part or limb having a generally cylindrical shape is to be covered by the venting material.

The use of a flexible plastics material such as EVA or similar waterproof material is quite advantageous when the material is formed not only with the aforementioned channels or grooves 30 but also with the recesses 22 as these recesses also enable the material to be stretched or elongated around a limb or body part. Further, the recesses 22 allow more skin area to be exposed to air, thereby increasing the comfort of the user/patient. Assuming that the recesses are not flattened by the stretching process, there will be air in the recesses and, moreover, this air can be renewed or refreshed while the cast is being worn due to the presence of the holes 26, some of which penetrate through the substrate in the region of the recesses (see the holes indicated at 36 in FIG. 2b). Another advantage of the recesses 22 is that they facilitate the growth of hair on the skin covered by the venting material. Also, they reduce the contact area between the skin and the EVA material which increases the ability of the skin under the venting material to maintain a healthy state.

Figure 3:
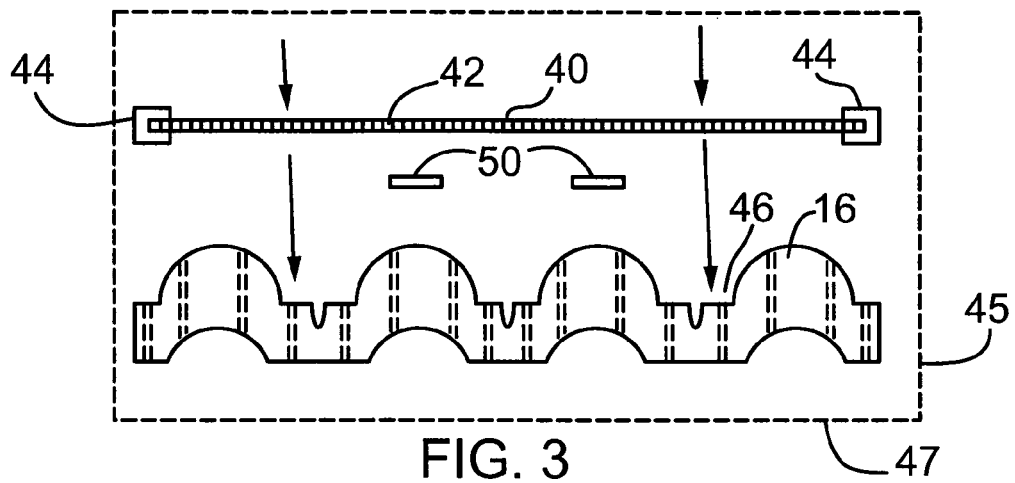
FIG. 3 is an exploded view showing portions of layers of materials that can be applied around a patient's limb prior to application of a surgical cast, these layers including the venting material of FIGS. 2a and 2b and a surrounding stockingnet.
Figure 4:
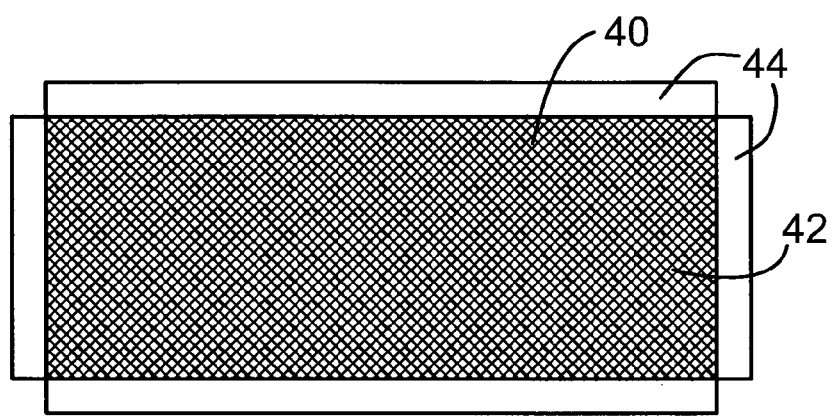
FIG. 4 is a plan view of a mesh that can be applied over the cast venting material of FIGS. 2 and 3.

Illustrated in FIGS. 3 and 4 and also shown in FIG. 6 is a thin layer of flexible mesh 40 which in an exemplary application of the above described venting material is extended over the second side having the protrusions. This mesh is formed so as to have numerous, very small apertures 42 formed therein, these apertures being sufficiently small to prevent surgical cast forming material from filling air gaps between the protrusions 24 and from filling or blocking the small holes 26 when the surgical cast is being formed. In an exemplary form of the mesh, its edges are covered with a protective edge trim 44 which can be made of a suitable, flexible, soft plastics material such as EVA. The edge trim has the effect of making the mesh easier and more comfortable to use and prevents the mesh from having sharp or uncomfortable edges. In an exemplary form of the mesh itself, it is very thin (about 0.3 mm) and is therefore flexible. The mesh can be formed if necessary into a particular shape by thermoforming. The mesh can be made from a suitable plastic or metal. If the mesh is used in combination with an overlying or surrounding stockingnet material, both the mesh and the stockingnet will help to prevent the wet cast material from filling the wide gaps 46 between the protrusions and from filling the grooves 30. The mesh can optionally be either attached to the underlying venting material 16 or it can be unattached so that it can slide freely on top of the venting material. Leaving the mesh unattached can be advantageous if the venting material is covering a body part or limb having a relatively simple, cylindrical shape. In this case, the mesh generally needs to be bent in only one direction to conform to the shape of the venting material. It is possible to attach the mesh 40 to the venting material 16 by means of double sided tape 50 which per se is of standard construction. The pieces of tape 50 can be small, for example, 1 cm×1 cm each. If the tape 50 is used, it is placed in the region of the longitudinal center of the mesh section. This allows the venting material to stretch and bend under the mesh layer while at the same time maintaining the mesh in the desired position relative to the venting material. As shown in FIG. 3, a tube of stockingnet 45 can be used to hold the mesh 40 in place on top of the venting material. The stretchable, elastomeric material of the stockingnet can be pulled and stretched to place it over these two layers and then it will contract to hold the mesh in place. The inner side 47 of the stockingnet extends over the inside surface on the first side of the substrate forming the venting material.

Figure 5:
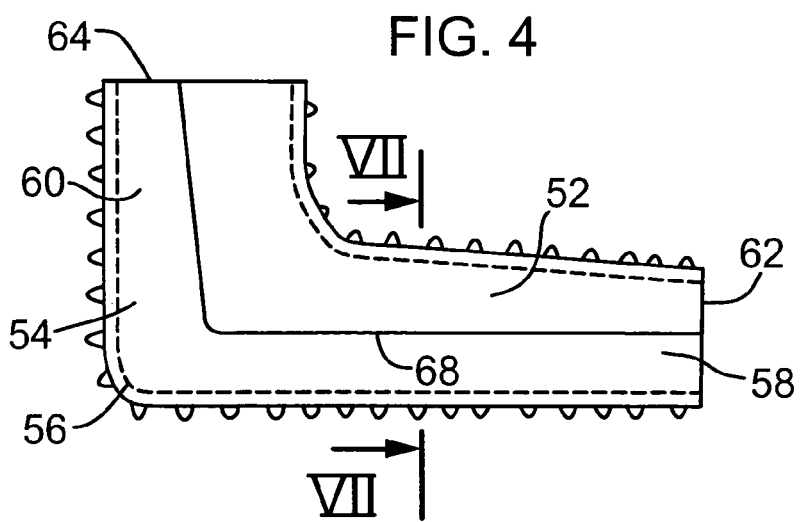
FIG. 5 is a schematic side view of two half sections of molded venting material adapted to fit around a patient's elbow, this view omitting many of the protrusions distributed on the surface of the half sections for ease of illustration.

Instead of using an elongate strip of venting material that is wound in a spiral about a limb or body part to provide venting, the venting material can also be cut or molded into sections adapted to fit around the body part or limb. The use of fitted sections of venting material can be particularly useful to cover body sections such as a foot or hand that can be difficult to cover uniformly and in a snug fitting manner by means of a spirally wound strip of venting material. FIG. 5 illustrates the use of two half sections 52, 54 which have been molded or otherwise formed to fit around a person's elbow. The half section 52 is formed to fit around the inside corner of the elbow and to extend part way along the forearm and part way up the upper arm. The half section 54 covers the outside corner of the elbow at 56 and also extends part way along the forearm by means of end section 58 and part way along the upper arm by means of end section 60. The two half-sections 52, 54 both extend to a first end 62 and to a second end 64 of this venting device and they meet along two longitudinal joints 66, 68 with only the joint 68 being visible in FIG. 5. In an exemplary version of the half sections 52, 54 and as illustrated in the cross-section of FIG. 7, the joints 66, 68 are formed by wedge shaped or tapered longitudinal edges on each of the half sections 52, 54. Thus, the section 54 has wedge shaped edges at 70, 72. The edge 70 overlaps wedge-shaped edge 74 of the section 52 while the edge 72 overlaps the wedge-shaped edge 76. These wedge-shaped edges can provide for a smoother transition between the sections or, in other words, a smoother joint which is less likely to cause discomfort. The overlapping edges can be connected to one another in any of several different ways with the primary criteria being comfort to the patient. For example, it is possible to use a suitable strip of tape that will adhere to the venting material and that extends along the joint or it is possible to use a suitable adhesive.

Another way of connecting the overlapping edges is illustrated in the detail view of FIG. 8 which shows two adjacent sections of venting material 16 at 80 and 82. In this case, the wedge-shaped edge strips 84, 86 are connected to their respective substrates by means of a line of zig-zag stitching 88 which extends along the joint for the length of each edge strip. Arranged on the sloping, inner surfaces of the edge strips 84, 86 are strips of hook and loop type fasteners 90, 92. Fasteners of this known type are commonly sold under the trademark VELCRO. As is well know, one of these strips 90, 92 has numerous, small hooks formed thereon while the other strip has numerous small loops formed thereon. An advantage of this type of fastener is that it can readily be cut to the required size and it is completely detachable as well as being adjustable. Although it is possible for the edge strips 84, 86 to be made of a different, flexible material than the adjacent venting material sections 80, 82, the edge strips 84, 86 can be made of the same material, for example, EVA.

FIG. 1 also illustrates the use of similar wedge-shaped edge strips 94, 96 to connect together adjacent ends of cast venting devices, each formed of two half sections as described above. One of these cast venting devices covers an elbow portion of the patient's arm and it is indicated at 98. This venting device is similar to that described above in connection with FIG. 5. A straight, tubular venting device 100 is used to cover the wrist region and part of the forearm. The two half-sections which form the device 98 each have an edge strip 94 attached thereto at one end and the two half sections which make up the venting device 100 each have an edge strip 96 attached thereto. Again, these edge strips 94, 96 can be attached by hook and loop or VELCRO™ type fasteners, if desired. The use of the wedge-shaped connecting strips 94, 96 facilitates a smooth transition between the two venting devices 98, 100 and further facilitates some adjustment of the adjacent ends of these devices relative to each other. It will be appreciated that the two wedge-defining surfaces 101, 102 of each edge section or edge strip extend at a small acute angle to one another and, in an exemplary version of these edge strips, this acute angle does not exceed 30 degrees.

FIG. 1 also illustrates how air is able to enter and exit the space created by the venting devices 98, 100 under the cast 14. In particular, air is able to enter into or exit from the annular opening at 104, in this case, the opening surrounding the hand which is only partially covered by the cast 14. This air flow is indicated by the two way flow arrows A in the figure. Similarly, air is able to enter into or exit from the annular opening 106 at the opposite end of the cast 14. Because of the presence of the protrusions 24 as well as the mesh 40 which covers these protrusions, there is an air gap 108 created between the inside of the cast and the outer surfaces of the venting devices and this air gap not only extends the length of the cast but also completely around the arm or other limb. In addition, this circulating air is able to reach the surface of the patient's skin by means of the numerous holes 26 through the venting material and the recesses 22.

FIG. 6 illustrates not only the use of an elongate strip of venting material which has been wound in a spiral fashion about a patient's arm but also the use of a tubular stockingnet 110 which is an optional feature that can be used either instead of the mesh 40 or in combination with the mesh 40. The stockingnet can be formed as one piece and can extend the entire length of the cast which is to be formed on the patient's limb or body. As the stockingnet is both stretchable and flexible, it can be made to fit closely about the exterior of the cast venting material, including any overlying mesh 40. As the use of such flexible tubes is known in the art, a detail description of its use and construction herein is deemed unnecessary. Reference can, for example, be made to applicant's U.S. Pat. No. 7,250,034 issued Jul. 31, 2007 which illustrates and describes a tube of this type. The description and drawings of this US patent are incorporated herein by reference. One type of flexible tube suitable for this purpose is that sold under the trademark SURGILAST. Provided that the holes in the stockingnet are sufficiently small, both the stockingnet itself and the mesh 40 beneath it can help prevent cast forming material from filling the air gap between the venting material and the mesh. The use of stockingnet is particularly desirable when the venting material is in the form of an elongate strip wrapped around the limb or body part as it helps to keep the adjacent spirals of the venting material in place as well as to hold the mesh 40 in position over the spirals.

Figure 11:
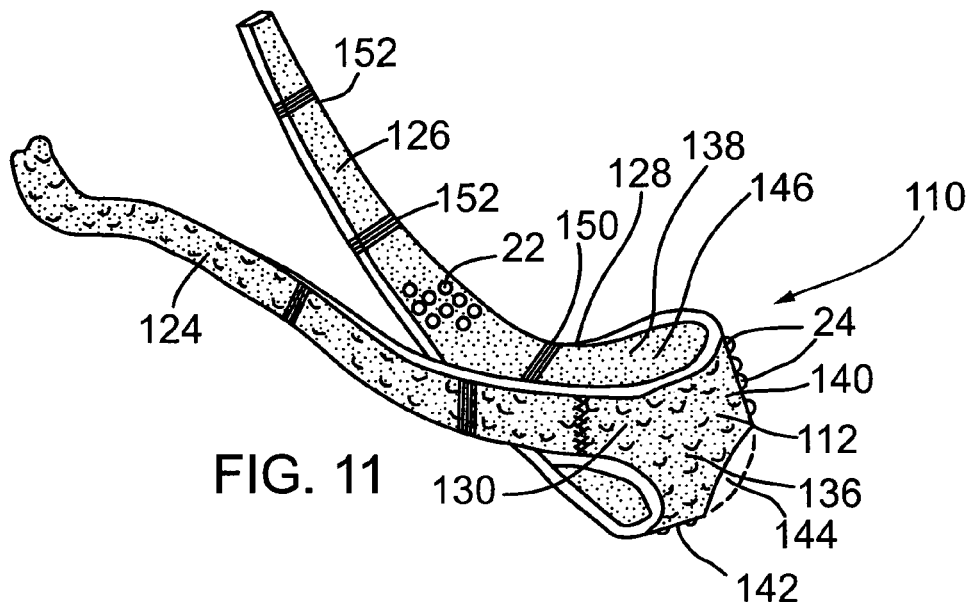
FIG. 11 is a perspective view of a surgical cast venting device for venting a region of a patient's limb which includes a bent section.
Figure 12:
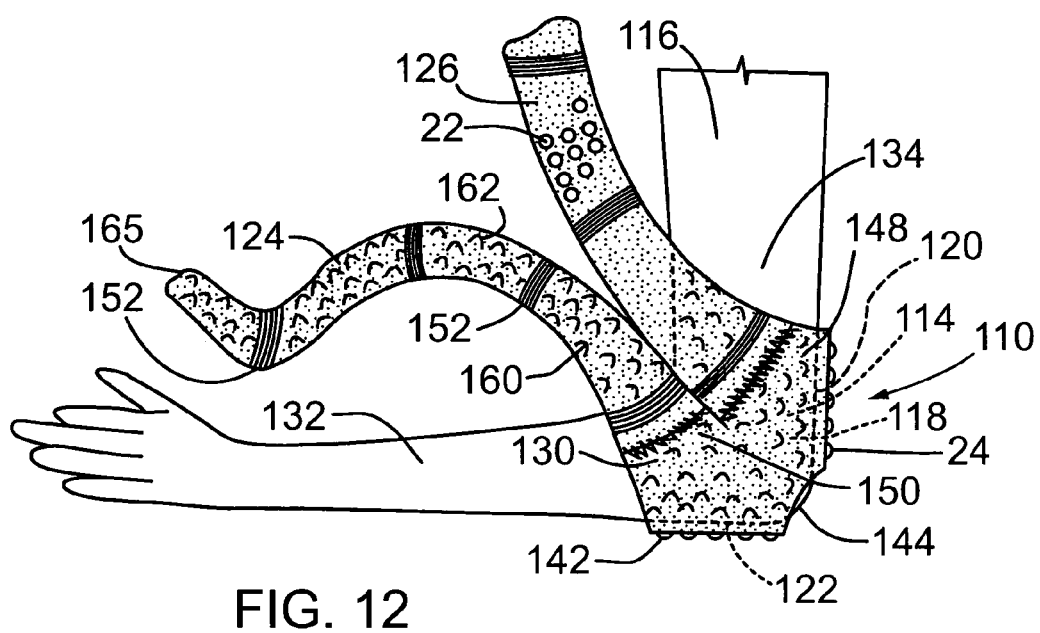
FIG. 12 is a side view showing how the venting device of FIG. 11 can be attached to a patient's arm in order to cover an elbow and adjacent sections of the arm.

Turning now to another embodiment of a venting device for a surgical cast, this embodiment is illustrated in FIGS. 11 to 14 and is intended for venting a region of a patient's limb which includes a section of the patient's limb having a bend therein. The venting device 110 has a flexible, main central portion 112 adapted to cover a major part of a first section 114 of the patient's limb which has the bend therein. As illustrated in FIG. 12, this bend can be formed at an elbow of a patient's arm 116. The central portion 112 as shown in FIG. 12 is able to cover opposite side surfaces of the limb, including side surface 118 and a front or rear surface extending between the side surfaces. In the case of the illustrated venting device constructed to cover an elbow, the venting device covers a rear surface of the elbow indicated at 120 and a bottom surface. In the case of a venting device intended to cover and fit on a bent knee or ankle, for example, the central portion may be constructed to cover a front surface of the knee area or a rear surface of the ankle/heel area.

Figure 14:
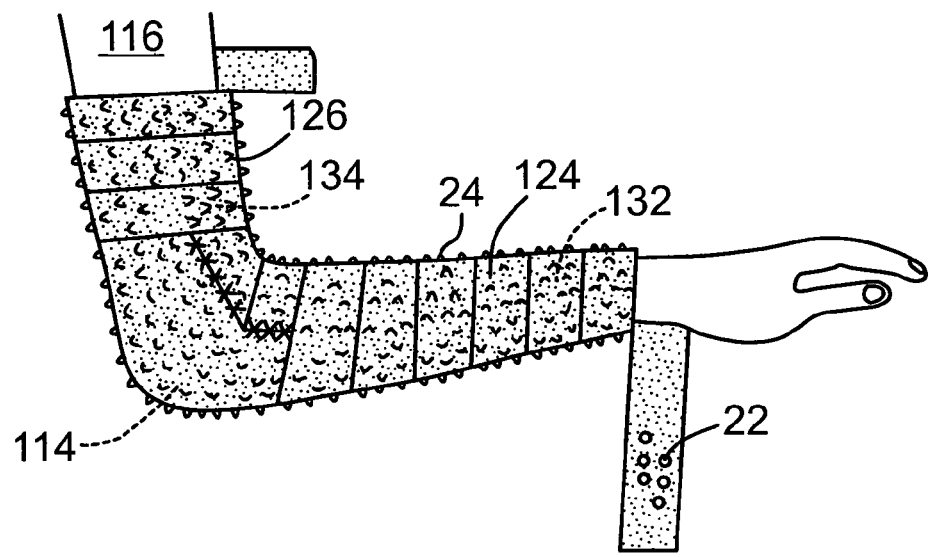
FIG. 14 is a side view similar to FIG. 12 but showing the venting device substantially attached to the patient's arm with the two connecting strips wrapped around the forearm and the upper arm.

The venting device 110 also has two elongate, flexible connecting strips 124, 126 extending from and connected to two corners of the central portion located on opposite sides of the central portion. These corners are indicated at 128 and 130 in FIG. 11. Each of these strips 124, 126 is adapted and arranged to be wrapped in a spiral manner as shown in FIG. 14 around a respective one of second and third sections of the patient's limb, these second and third sections being located at opposite ends of the first section 114 and adjacent thereto. In the case of connecting strip 124, it is wrapped around a second section of the arm comprising at least part of the forearm at 132 while the connecting strip 126 is wrapped around a third section 134 comprising part of the upper arm. The central portion 112 has at least a first side 136 and an opposite second side 138. These first and second sides during use of the venting device are positioned on opposite sides of the first section 114 of the patient's limb in order to provide ventilation thereto. Thus, these sides are formed to permit air circulation under a surgical cast that is formed over the venting device 110, this cast not being shown in the drawings but being of standard construction. The cast is formed over the venting device when the venting device has been arranged on the first, second and third sections of the patient's limb so as to substantially cover at least the major part of the first section of the limb. As illustrated by FIG. 11, the exemplary form of the device also has a first end wall 140 which can be concavely curved on its inner side and a second end wall 142. These two end walls connect the first side 136 to the side wall 138 and these walls can be integrally formed as a single substrate of flexible material or can be connected to each other by suitable stitching (not shown). Optionally, the central portion can have a relatively large aperture 144 formed therein between the first and second sides, this aperture being located on an outer side of the bend in the patient's limb during use of the venting device and provided to accommodate the bend in a comfortable manner. Alternatively, the central portion can be formed as a single, continuous substrate of venting material, without the aperture 144.

The central portion 112 and the connecting strips 124, 126 are made of a waterproof, flexible substrate formed of a plastics material and having an inner side 146 and an outer side 148. This flexible substrate can in fact be the same flexible venting material as the material 16 described in detail above in conjunction with FIGS. 1, 2a and 2b. The inner side thus has a plurality, shallow, concave recesses 22 (only some of which are shown in FIGS. 11, 12 and 14 for ease of illustration) located over the device and the outer side 148 has a plurality of the protrusions 24 distributed over the substrate forming the device. It will be understood that these recesses and protrusions help to provide air circulation during use of this venting device and, as in the case of the venting material 16, the outer side 148 with its protrusions can be covered by a mesh suitably cut and shaped to fit snugly to the exterior of the device.

In the illustrated venting device 110, the two strips are connected to the central portion 112 by means of stitch lines 150 which can comprise zig-zag stitches. Also, each of the connecting strips can be integrally formed with at least one series of corrugations 152 which extend transversely across the respective connecting strip. In the embodiment of FIGS. 11 and 12, each strip 124, 126 is provided with two or three series of corrugations. Each of these series enhances the ability of the respective strip to bend in a transverse direction in a plane extending parallel to the two opposite sides of the respective strip where the series of corrugations is located. These corrugations provide at least a couple of advantages as compared to connecting strips not having these corrugations. Firstly, the corrugations increase the ability of each strip to be stretched or elongated as may be required when the strip is being wound around a patient's limb, the stretching process helping to keep the connecting strip tight and snug on the limb. Secondly, as indicated, each series of corrugations enables adjacent sections of the strip which are separated by the corrugations to bend relative to one another in the transverse direction. Thus, the first section 160 of the connecting strip 124 can extend at a different angle than the second section 162 because the corrugations 152 can be pulled out or stretched at one end more than the other end. This transverse bending ability increases the ability of the strip to wrap snugly around the limb or body part.

Figure 13:
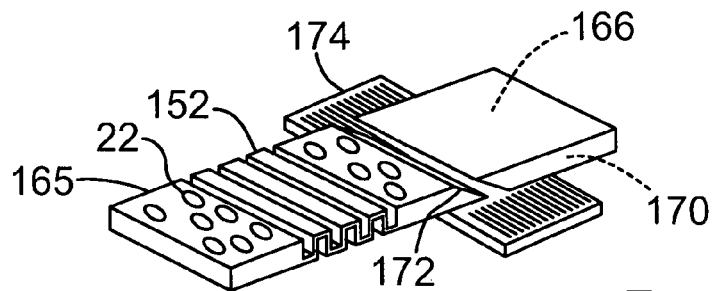
FIG. 13 is a detail view showing how an extension section of the venting device of FIGS. 11 and 12 can be added using elastic tape.

FIG. 13 illustrates how an extension strip 165 which can include a series of corrugations 152 as shown to an end section 166 of one of the connecting strips 124, 126. In particular, adjacent ends of the extension strip 165 and the connecting strip can be wedge shaped as indicated at 170 and 172. The wedge shaped ends can be connected together by means of an elastic adhesive covered band 174 which is able to stretch with the EVA material. Alternatively zig-zag stitching can be used to attach the wedge-shaped edges or a suitable adhesive material.

In one exemplary embodiment of the venting device 110, the two connecting strips 124, 126 at least are covered on their outer surfaces with thin mesh layers similar to that shown in FIGS. 3 and 4, these mesh layers being held in position by tubes of stockingnet material (not shown) similar to the above described stockingnet 45. Thus in this venting device also, the surgical cast venting material is substantially prevented from filling the gaps formed between the protrusions 24. If desired, mesh material can also be applied over the exterior of the central portion 112 of the device and held in place by double-sided tape, for example.

FIGS. 1, 9a, 9b and 10 illustrate one embodiment of a device for supporting a fractured limb of a patient, this device being indicated generally at 180. The device 180 can usefully be employed in combination with the above described venting materials and venting devices under a rigid cast. The supporting device includes two supporting plates 182, 184 adapted to and sized to support a fractured limb of a patient on one side of the fracture prior to application of a surgical cast. In an exemplary version of each of these plates, the plate has an inside surface 186 which is contoured so as to have a concave shape (see FIG. 10) substantially matching the contour of the fractured limb in the region of the fracture and on the side of the fracture where the supporting device is to be used. Because a leg or an arm generally has a convex surface as seen in transverse cross-section, each supporting plate is formed with a matching concave curve, as shown, this curve extending transversely across the plate. When used in combination with a venting material substrate as shown in FIG. 1, the supporting device 180 is placed against the exterior of the venting material substrate so as to press against the protrusions 24. Thus, the contour of the inside surface of the supporting plates can in fact be matched to the exterior contour of the shaped venting material.

The two plates 182, 184 are adjustably connected together by means of a connector 190 which can be a threaded connector such as a suitable screw having a threaded shank and a head engagable with a tool such as a screw driver. The connector is movable from a locked position where no relative movement between the supporting plates occurs and an adjusting position which allows relative pivotal movement between central longitudinal axes of the supporting plates, these axes being indicated at $A_1$ and $A_2$ in FIG. 9a. During use of the supporting device, a surgical cast can be formed around the supporting device and the fractured limb while the supporting device is rigidly secured to one side of the fractured limb with the connector in the locked position (see FIG. 1). Although it will be readily apparent that the two supporting plates can be pivotably connected in various ways, according to one form of connection, one of the supporting plates, for example, the plate 182, is formed with a cylinder or sleeve 192 which can be integrally connected or otherwise connected to the inside end of the plate. Through this sleeve extends a first transversely extending passage through which the screw or connector 190 extends and from which a threaded shank of the screw extends. The other supporting plate, for example, the plate 184, is also formed with a cylinder or sleeve 194 which is coaxial with the sleeve 192 for attachment purposes. The two sleeves can be formed with interlocking or telescoping adjacent ends to help hold them in a properly aligned position when they are being attached with the screw. The sleeve 194 forms a second, transversely extending passage which is threaded to receive the threaded shank of the screw or connector. It will be understood that by tightening the screw, the adjacent sides of the two sleeves can be clamped together to hold the two supporting plates in a selected position suitable for supporting the fractured limb.

Shown in FIGS. 9b and 10 is the outer surface of each of the plates 182, 184. In order to render the plates sufficiently rigid to support the limb, the surface can have formed thereon a series of parallel and criss-crossing ribs 198. Also, extending along each side edge of each supporting plate is an edge flange 200 which, as shown in FIG. 1, can taper towards the outer end 202 of the plate. The opposite inside surface 186 of each supporting plate is made smooth so that the supporting device will not be uncomfortable for a patient when worn. The width of the supporting plates can vary depending upon their particular use or application but, in one exemplary embodiment of the device, the plates have a width of approximately 2 inches, this width being suitable for use of the device on a fractured arm.

As shown in FIG. 1, the supporting device 180 can be secured in place by means of straps 204, 206 attached to both of the supporting plates and sufficiently long to wrap around and be secured to the fractured limb. If desired, there can be a pair of straps attached to each supporting plate as shown in FIGS. 9a and 9b, with each of the straps extending from a respective side of the plate. Alternatively, a single long strap having a length sufficient to extend around the adjacent limb can be used. Although it is possible to secure the strap or straps in a variety of ways, in one exemplary version of these straps, they are either fitted with or comprise hook and loop type fasteners which, as indicated, are commonly sold under the trade-mark VELCRO. These fasteners or fastener strips are used to detachably connect either adjacent ends of two strips together in order to secure the supporting device to the fractured limb or to secure the free end of a single long strap to the side or edge of the supporting plate.

Figure 15:
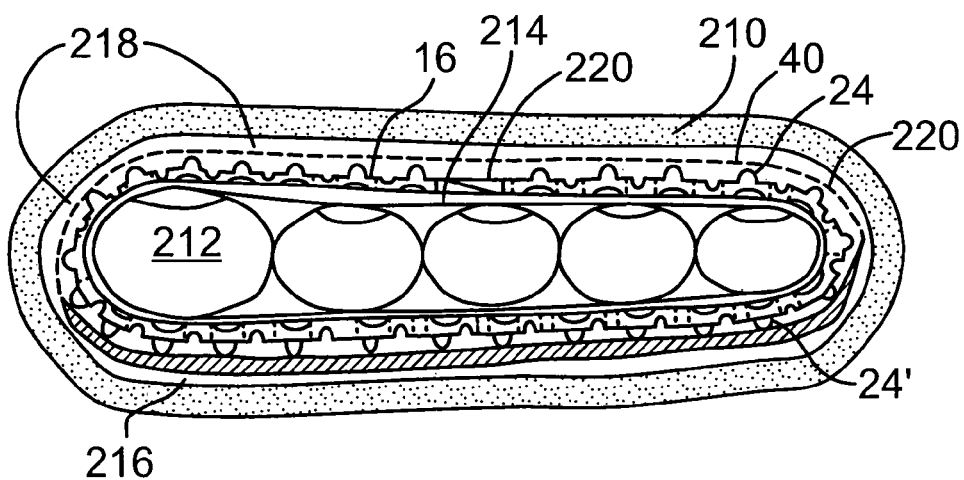
FIG. 15 is a schematic, transverse cross-section showing how venting material constructed in accordance with the invention can be used to enclose a patient's foot and toes for purposes of a cast covering the foot region.

Turning now to the application for the present cast venting material shown in FIG. 15, this figure illustrates a rigid cast 210 extending around a patient's foot which is indicated by the illustrated toes 212. It will be understood that the cast 210 can extend not only over part or all of the foot but also over the patient's ankle and part of his or her leg. In the illustrated application, the foot is surrounded initially by a relatively soft, absorbent cotton fabric or gauze 214. Such a material can be used whenever the present cast venting material is used, if desired, in order to increase the comfort of the patient. Extending over the cotton fabric is the venting material 16 which can be constructed as described above in conjunction with FIGS. 1, 2a and 2b. Its protrusions 24 extend outwardly away from the foot while its recesses 22 face the cotton fabric. Optionally, and in a known manner, the underlying venting material can be supported by and rest against a rigid sole plate 216 which extends the width and length of the foot and which can be contoured to the patient's foot. The use of such a sole plate in a walking cast is illustrated and described in applicant's published Canadian patent application No. 2,478,162, the drawings and description of which are incorporated herein by reference. The plate can be made of metal or a suitably rigid plastics material and it helps to protect both the foot (which may be fractured) and the cast (by spreading the user's weight over the rigid cast material). If the optional plate 216 is used, there is no need for the adjacent venting material to be covered by the above described mesh 40. However, extending over the top of the foot and over the upper section of the venting material is the above described mesh 40 which can be a thermoformed mesh. Opposite side sections 218, 220 of the mesh extend down to the edges of the sole plate 216 and can be connected thereto, if desired. Again, the mesh 40 acts to prevent wet cast material from blocking or filling the network of air gaps between the protrusions 24.

Optionally, the protrusions 24 in the region underneath the foot, these being indicated at 24', can be made of a harder plastics material along with the adjacent layer or substrate of venting material to which they are integrally connected. Thus, in an exemplary version of the venting material, for most applications the hardness of the material ranges from 18-25 DURA but the hardness of the EVA material forming the protrusions 24' and the adjacent substrate can be 30 DURA or more. By providing protrusions made of a harder yet flexible material, the air passages or gaps between the protrusions are not collapsed when the patient's weight is placed on the foot.

FIG. 15 also illustrates wedge shaped edges at 220 where opposite longitudinal edges of the substrate can be connected to each other. Again, the wedge edge sections can be fitted with VELCRO™ for attachment purposes, as described above.

Figure 16:
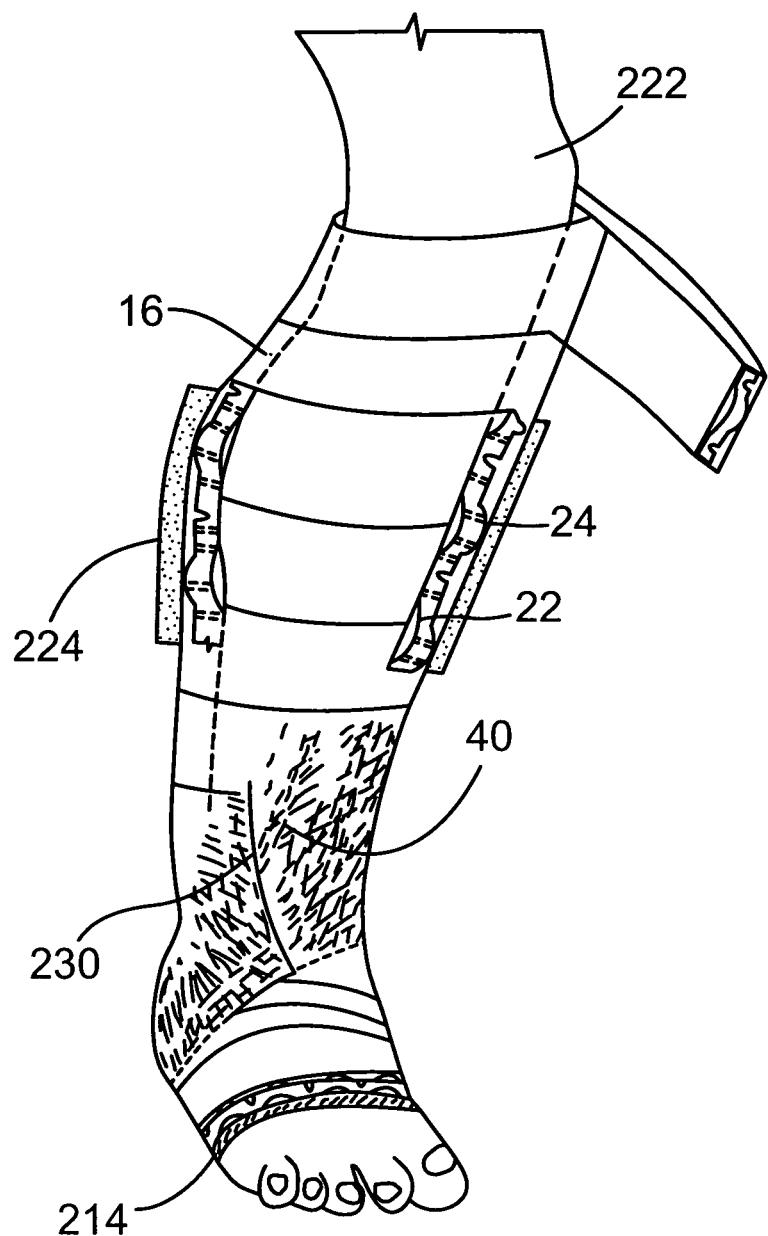
FIG. 16 is a perspective view, partly in cross-section, illustrating how venting material constructed in accordance with the invention can be used on a patient's leg and foot.

FIG. 16 illustrates the possible use of the present cast venting material on a lower leg, that is the portion of the leg below the patient's knee 222. In this figure, the venting material 16 has been wrapped in a spiral fashion around the leg. A portion of the rigid cast is shown at 224. Located between the cast and the venting material is a thermoform mesh 40 only a portion of which is shown in the ankle area. Again, if desired, the venting material can extend over a layer of cotton fabric or gauze, this material being indicated at 214. Although not shown in the figure, there can be an overlying layer formed by a tubular stockingnet, this layer being on top of and adjacent to the mesh 40. The elastic stockingnet rests against the exterior of the mesh and helps to hold it in position as well as holding the venting material in position. It will be understood that the mesh sections can be thermoformed in sections which are generally semi-circular in transverse cross-section and which are formed to match the exterior shape of the underlying venting material. These semi-circular sections of mesh meet along a joint line indicated at 230.

Figure 17:
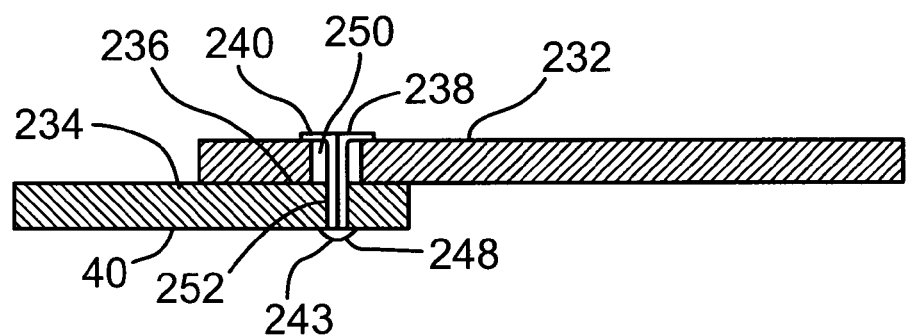
FIG. 17 is a cross-sectional detail showing the adjustable connection between two mesh sections.
Figure 18:
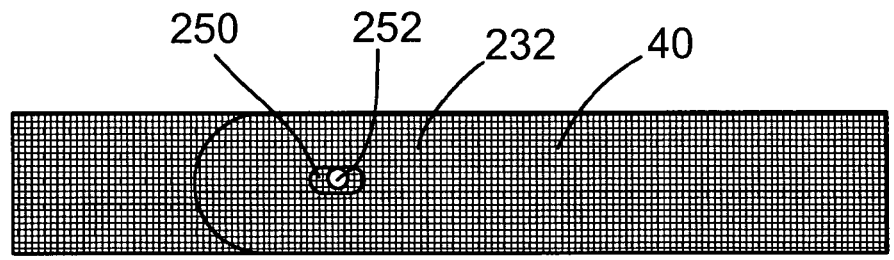
FIG. 18 is a top view of end portions of the adjustable mesh sections of FIG. 17, this view omitting the pin connector for illustration purposes.

FIGS. 17 and 18 illustrate how adjacent sections of the mesh 40 can be attached in an adjustable manner by means of a pin 243. It will be understood that the overall length of two or more mesh sections may need some final adjustment even after their initial forming and cutting. In addition, the angular relative position of two adjacent mesh sections may need to be adjusted or changed to accommodate the changing dimensions or curvature of the underlying venting material and body part. FIG. 17 shows how adjacent end sections 232, 234 of the mesh can be overlapped at 236 and pivotably connected by means of the pin 243, which can be in the form of a cotter pin having two separable tines 238, 240 and a head 248. To allow some longitudinal adjustment one end section 232 can be formed with an elongate slot 250. The other end section 234 has a circular hole at 252 through which the tines are pushed before separation of their end sections as shown. The head and the tines should be made as small as possible so as not to cause discomfort to the cast wearer.

It will be appreciated that various modifications and changes can be made to the described and illustrated embodiments of the invention without departing from the spirit and scope of the invention. Accordingly, all such modifications and changes as fall within the scope of the appended claims are intended to be part of this invention.

What I claim is:

1. A surgical cast venting device for venting a region of a patient's limb which includes a first section of the patient's limb having a bendable joint therein, said venting device comprising:

a flexible wide, central portion sufficiently large in area to cover a major part of said first section of the patient's limb having said bendable joint therein including opposite side surfaces of the limb and a front or rear surface extending between said side surfaces; and two elongate, flexible wrapping strips extending from and connected to opposite sides of said central portion, each strip being sufficiently long to be wrapped in a spiral manner around a respective one of second and third sections of the patient's limb, said second and third sections being located at opposite ends of said first section and adjacent thereto, wherein said central portion has at least a first inside surface and a second outside surface, said first and second strips during use of the venting device being wrappingly positioned on opposite sides of the first section of the patient's limb, one of said first and second surfaces formed therein generally uniformly spaced circular protrusions to permit air circulation under a surgical cast that is formed over said venting device when said venting device has been arranged on the first, second and third sections of the patient's limb so as to substantially cover at least said major part of said first section of the patient's limb.

2. A surgical cast venting device according to claim 1 wherein said central portion comprises a substrate made of a waterproof, flexible plastic material having an inner side and an outer side, said inner side having a plurality of shallow, concave recesses distributed over the substrate and the outer side having a plurality of protrusions distributed over the substrate, said central portion being preformed with a concave contour to receive said bendable joint.

3. A surgical cast venting device according to claim 2 wherein said plastics material is ethyl vinyl acetate (EVA) and has a thickness of about 3 mm prior to said plastics material being molded to form said recesses and protrusions and said substrate is perforated with a plurality of small holes distributed over both said central portion and said connecting strips, said small holes allowing air to pass through said substrate during use of the venting device under a surgical cast.

4. A surgical cast venting device according to claim 1 wherein each of said connecting strips is integrally formed with at least one series of corrugations which extend transversely across the respective connecting strip, each of said series enabling its respective strip to bend in a transverse direction in a plane extending parallel to the two opposite sides of the respective strip where the series of corrugations is located.

5. A surgical cast venting device according to claim 1 wherein each connecting strip is connected to said central portion by a stitch line.

6. A surgical cast venting device according to claim 1 wherein said central portion has an aperture formed therein between said first and second sides, said aperture being located on an outer side of the bend in the patient's limb during use of the venting device and provided to accommodate said bend.

7. A surgical cast venting device according to claim 2 including a thin layer of flexible mesh extending over an outer side of each of said connecting strips and having numerous apertures formed therein, said apertures being sufficiently small to prevent surgical cast venting material from filling gaps formed between said protrusions, and also including a tube of stockingnet extending around each connecting strip and its respective layer of mesh.

8. A surgical cast venting device for use as an underlayer for a surgical cast on a jointed limb comprising:

a wrappable substrate made of a waterproof flexible plastic configured to wrap around a human limb and having inner and outer surfaces, said inner and outer surfaces having shallow generally circular recesses and overlying raised generally circular protrusions, respectively, formed thereover;

said substrate having a wide central portion which is concavely contoured and joined to oppositely extending wrapping strap portions, each of said wrapping strap portions being narrower than said central portion and having stretchable corrugations formed crosswise therein and being of sufficient length as to fully encircle said limb multiple times;

whereby said substrate may be wrapped as an underlayer to a cast around the jointed limb with the central portion surrounding the joint and the wrapping portions extending wrappingly away from said joint in opposite directions.

9. The device as defined in claim 8 wherein the central portion has an aperture formed therein to expose a portion of the jointed limb when in use.

* * * * *